United States Patent [19]

James et al.

[11] Patent Number: 4,499,154

[45] Date of Patent: Feb. 12, 1985

[54] DIPPED RUBBER ARTICLE

[75] Inventors: Michael H. James, Flamstead; David M. Bratby; Roger Duck, both of London, all of England; Howard I. Podell, 28 Beachfront La., New Rochelle, N.Y. 10805; Albert Goldstein, Tinton Falls, N.J.; David C. Blackley, Chesham, England

[73] Assignee: Howard L. Podell, New Rochelle, N.Y.

[21] Appl. No.: 445,436

[22] Filed: Nov. 30, 1982

[30] Foreign Application Priority Data

Sep. 3, 1982 [GB] United Kingdom ............... 8225200

[51] Int. Cl.$^3$ ............................................. A41D 19/00
[52] U.S. Cl. .................................... 428/494; 428/521; 2/167; 2/168; 2/DIG. 7; 128/132 R; 427/133
[58] Field of Search ............... 428/515, 521, 494; 2/167, 168, DIG. 7; 128/132 R

[56] References Cited

U.S. PATENT DOCUMENTS

| | | | |
|---|---|---|---|
| 2,621,333 | 12/1952 | Thomas et al. | 2/168 |
| 3,411,892 | 11/1968 | Kavalir et al. | 428/494 X |
| 3,728,739 | 4/1973 | Semp | 2/168 |
| 3,745,042 | 7/1973 | Lim et al. | 427/384 X |
| 3,813,695 | 6/1974 | Podell, Jr. et al. | 2/168 |
| 3,856,561 | 12/1974 | Esemplare et al. | 428/494 |
| 3,872,515 | 3/1975 | Miner et al. | 2/168 |
| 3,919,442 | 11/1975 | Esemplare et al. | 428/494 |
| 3,959,554 | 5/1976 | Hick | 428/336 |
| 4,064,564 | 12/1977 | Casey | 2/168 |
| 4,082,862 | 4/1978 | Esemplare et al. | 428/494 X |
| 4,100,309 | 7/1978 | Micklus et al. | 427/2 |
| 4,143,109 | 3/1979 | Stockum | 264/112 |
| 4,302,852 | 12/1981 | Joung | 2/167 |
| 4,304,008 | 12/1981 | Joung | 2/167 |
| 4,310,928 | 1/1982 | Joung | 2/168 X |

FOREIGN PATENT DOCUMENTS

| | | |
|---|---|---|
| 1434453 | 3/1965 | France . |
| 1453817 | 8/1966 | France . |
| 2193710 | 7/1972 | France . |
| 2297910 | 1/1976 | France . |

*Primary Examiner*—George F. Lesmes
*Assistant Examiner*—Nancy A. B. Swisher
*Attorney, Agent, or Firm*—Darby & Darby

[57] ABSTRACT

A skin-contacting coating of a lubricating hydrogel polymer bonded to a rubber article (such as a surgeon's glove) is treated by means of surfactant material (such as a bactericidal cationic surfactant which preferably has an N-hexadecyl group) or a long chain fatty amine so as to substantially improve the lubricity of the coating with respect to damp skin.

The hydrogel polymer is preferably a copolymer of 2-hydroxyethylmethacrylate (HEMA) with methacrylic acid (MAA) or with 2-ethylhexyl acrylate (EHA) or with both MAA and EHA. The copolymer contains HEMA and MAA is a molar ratio of 1 to 10:1 of HEMA and EHA in a molar ratio of 2.5 to 10:1. Such a hydrogel polymer has improved lubricity to dry skin and, if used for this purpose, need not be treated with a surfactant or fatty amine to improve the lubricity with respect to damp skin.

9 Claims, No Drawings

DIPPED RUBBER ARTICLE

The present invention is concerned with flexible rubber articles and, in particular, thin-walled rubber gloves of the kind used by surgeons.

Surgeon's gloves are difficult to don and to facilitate donning a powdered lubricant, such as particulate epichlorhydrin-treated maize starch, is conventionally applied to the inner surface of the gloves. There is a risk of such powdered lubricant escaping from the interior of the glove to contaminate the surgical field, the lubricant escaping either during donning or, as sometimes happens, if the glove is punctured during an operation.

Proposals have been made for polymeric lubricant coatings which are bonded to the inner surface of such gloves and which, because they are bonded, cannot escape from the glove.

Examples of such proposals are in U.S. Pat. Nos. 4,070,713 and 4,143,109, which disclose gloves which have an inner layer of elastomeric material with particulate lubricant embedded therein, and U.S. Pat. Nos. 3,813,695, 3,856,561 and 4,302,852, which disclose surgeon's gloves with various polymeric slip coatings bonded to the inner surface thereof.

U.S. Pat. No. 3,813,695 ("the Podell patent") describes a surgeon's glove in which the glove material is formed of a laminate consisting of an outer layer of flexible material, for example rubber, and an inner layer of hydrophilic plastic material (such as a hydrogel polymer), the inner and outer layers being bonded together.

There are many known hydrogel polymers, examples of which are polyvinyl pyrrolidone, polyhydroxyethyl acrylate or methacrylate, polyhydroxypropyl acrylate or methacrylate, and copolymers of these with each other or with acrylic or methacrylic acid, acrylic or methacrylic esters or vinyl pyridine.

There are many disclosures of the coating of rubber articles, such as catheters and bathing caps, with such hydrogel polymers by dipping in a solution of a hydrophilic, hydrogel-forming polymer and curing the resulting polymer layer.

Examples of such disclosures include U.S. Pat. Nos. 3,326,742, 3,585,103, 3,607,473, 3,745,042, 3,901,755, 3,925,138, 3,930,076, 3,940,533, 3,966,530, 4,024,317, 4,110,495 and 4,125,477, and British Pat. Nos. 1,028,446 and 859,297.

Co-pending U.S. patent application No. 408,094 filed by Applicant Goldstein on Aug. 13, 1982, which is a continuation-in-part of abandoned Application No. 216,890 filed on Dec. 16, 1980, describes a hydrogel coating polymer and a process for applying the polymer to the inner surface of a vulcanised surgeon's glove.

We have evaluated many such hydrogel polymers and have surprisingly found that certain 2-hydroxyethyl methacrylate polymers provide superior lubricity with respect to dry skin and can be appropriately treated to provide superior lubricity with respect to damp skin.

According to the present invention, therefore, there is provided a flexible rubber article having bonded thereto a coating of a hydrogel polymer providing a skin-contacting surface of the article, said hydrogel polymer comprising at least one copolymer of 2-hydroxyethyl methacrylate (HEMA) with methacrylic acid (MAA) or with 2-ethylhexyl acrylate (EHA), or with both MAA and EHA; said copolymer containing HEMA and MAA in a molar ratio of at least 1:1 (such as 1 to 10:1) or HEMA and EHA in a molar ratio of at least 2.5:1 (such as 2.5 to 10:1).

The copolymer, which is preferably prepared by solution polymerisation (bulk polymerisation is less satisfactory), may be a binary copolymer of HEMA and either MAA or EHA, or it may be a ternary copolymer of these three monomers; a preferred such terpolymer has a monomer molar ratio of HEMA to (MAA+EHA) of 67:33 to 90:10 (that is 2 to 9:1) and a molar ratio of EHA to (HEMA+MAA) of 3:97 to 20:80 (that is 1: about 32 to 4).

Minor amounts of further monomers which do not impair the properties of the copolymer may be used in addition. A mixture of such copolymers can be employed, either with other such copolymers or with minor amounts of other polymers which do not impair the properties of the hydrogel.

The 2-hydroxyethyl methacrylate monomer used preferably has a low content of ethylene glycol dimethacrylate.

Copolymers as described above provide better lubricity with respect to dry skin than any other hydrogel polymer of the many we have evaluated; there is, however, a great difference between lubricity relative to dry skin and relative to damp skin. Since surgeons prefer to don their gloves after "scrubbing up", without fully drying their hands, their hands are distinctly damp. We have found that most hydrogel polymers used as bonded inner layers in surgeons' gloves, as suggested in the Podell patent, give totally inadequate lubricity as regards damp hands.

The coating of the hydrogel polymer of the article according to the invention is preferably cross-linked and surface treated (after cross-linking) with a physiologically acceptable surfactant or long chain fatty amine; this can enhance the lubricity of the layer with respect to damp skin. Such surfactants are preferably ionic; cationic surfactants are most preferred.

Preferred cationic surfactants are hexadecyl trimethyl ammonium chloride and N-cetyl pyridinium chloride, both of which significantly improve the lubricity with respect to damp skin without adversely affecting lubricity with respect to dry skin. When a fatty amine is used, it preferably has a hexadecyl group; an example of a suitable amine is N,N-dimethyl hexadecylamine (which is available commercially as Armeen 16D).

Cationic surfactants and fatty amines as described above improve the lubricity with respect to damp skin for a wide range of hydrogel polymers as well as the specific 2-hydroxyethyl methacrylate copolymers referred to above. According to another aspect of the invention, therefore, there is provided a flexible rubber article having a coating of hydrogel polymer bonded thereto to provide a skin-contacting surface of the article, in which the hydrogel polymer coating is surface treated with a surfactant or a long chain fatty amine, which is preferably bactericidal or bacteriostatic; preferred surfactants are cationic surfactants, particularly quaternized long chain fatty amines. Particularly preferred are quaternized amines having N-cetyl (N-hexadecyl) groups, such as the above-mentioned hexadecyl trimethyl ammonium chloride and N-cetyl pyridinium chloride. Preferred long chain fatty amines include amines having a hexadecyl group, such as N,N-dimethylhexadecylamine (for example, the above-mentioned Armeen 16D).

The use of such cationic surfactants serves to inhibit bacterial growth when the hydrogel layer is in contact with the skin; this is an advantage for surgeon's gloves because, as mentioned above, these are sometimes punctured during surgical procedures, and any bacteria which have grown on the surgeon's skin since commencement of the operation may be released into the surgical field.

The surfactant or fatty amine is generally used in the form of a solution, such as an aqueous solution (typically an aqueous solution containing at least 0.2% by weight, up to, for example, 2% by weight) of a cationic surfactant as just mentioned.

The hydrogel-coated article is preferably treated with a silicone liquid so as to reduce the surface tack on any surfaces not coated with hydrogel; this treatment is preferably carried out at the same time as treatment with a surfactant as mentioned above. It is preferred that treatment with a silicone (such as medical grade polydimethyl siloxane) is carried out with a bath containing at least 0.05% by weight of silicone (for example, 0.05 to 0.4% by weight).

The rubber used in the article according to the present invention may be a natural or synthetic rubber; natural rubber is preferred. It is also preferred that the article according to the invention should be formed (prior to bonding of the hydrogel layer thereto) by dipping of a rubber latex. The hydrogel layer is preferably applied to the rubber before vulcanization thereof; this has the surprising result that the skin-contacting surface has a much cooler feel. This may be because there is greater moisture vapor transmission through the final coated article.

An article according to the invention can be produced by a process comprising the steps of:

(a) forming a rubber article by dipping a former in a rubber latex, (b) leaching the rubber article in hot water, (c) priming the rubber surface of the article on the former, for example, by means of a dilute acid, (d) rinsing the primed surface in water or aqueous alkali, (e) dipping said article, while still on the former, in a solution of a hydrophilic, hydrogel-forming polymer and a curing agent therefor, (f) heat drying the resulting coating such that the resulting hydrogel polymer is bonded to said rubber, (g) vulcanizing the rubber and simultaneously curing the polymer by application of heat, (h) stripping the resulting article from the former, (i) applying a solution of surfactant material containing silicone to the article (for example, by tumbling in such a solution), optionally after washing, and (j) heat drying the resulting coating of surfactant material.

The application of the solution of surfactant material provides a substantially tack-free outer surface (that is, the surface not coated with hydrogel polymer), in addition to the inner surface, which is, of course, advantageous.

The rubber surface to which the hydrogel polymer is bonded may also be primed by dipping in, for example, a solution of an aluminum salt after priming with dilute acid.

The above process is also disclosed in U.S. patent application No. 445,470, filed on Nov. 30, 1982 (at the same time as this application) by two of the present inventors.

It is a feature of the present invention that the production of the dipped rubber article, leaching priming, application of hydrogel polymer layer, and vulcanization of the rubber and curing of the polymer can all be carried out in a continuous operation.

The present invention has been described primarily, with reference to surgeons' gloves; it is, however, applicable to other skin- or tissue-contacting flexible rubber articles, such as condoms, gloves used by doctors and veterinary surgeons for examination purposes (such gloves being often donned with dry hands), catheters, urethers, sheets and sheath-type incontinence devices.

When the present invention is used for articles such as urethers and catheters, the layer of hydrogel polymer is provided on the outer surface (this being the skin-contacting surface); for condoms the layer of hydrogel polymer may be provided on the inner surface and/or on the outer surface.

In order that the present invention may be more fully understood, the following Examples and Comparative Examples are given by way of illustration only.

EXAMPLE 1

A thin dipped surgeons glove of natural rubber latex was leached with sulfuric acid, rinsed, primed by dipping in aluminum sulfate solution, dried out completely and then dipped into a 4% alcoholic solution of a copolymer of 2-hydroxyethyl methacrylate (HEMA) and methacrylic acid (MAA) in a 1:1 molar ratio, followed by drying. The solution contained, in addition to the copolymer, 5 parts per hundred of partially methylated melamine-formaldehyde resin (as cross-linking agent) and 0.5 parts per hundred of paratoluene sulfonic acid (as catalyst).

The rubber was then vulcanized, after which the lubricity with respect to dry skin was subjectively evaluated on a scale of 1 to 5, in which:

1 means that the film is sticky
2 means that poor slip is obtained
3 means that moderate slip is obtained
4 means that quite good slip is obtained
5 means that excellent slip is obtained (comparable to the use of a powdered surface).

The dry skin lubricity number was 5; the coating adhered satisfactorily to the rubber and no visible flaking was observed.

EXAMPLES 2 to 11

Example 1 was repeated, except that the copolymer was replaced by the polymers indicated in the following Table 1:

TABLE 1

| Example No. | Polymer | Molar ratio of monomers | Dry skin lubricity number |
|---|---|---|---|
| 2 | HEMA/MAA | 2:1 | 5 |
| 3 | HEMA/MAA | 5:1 | 5 |
| 4 | HEMA/MAA | 10:1 | 5 |
| 5 | MEMA/EHA | 2.5:1 | 5 |
| 6 | HEMA/EHA | 4:1 | 5 |
| 7 | HEMA/EHA | 5:1 | 5 |
| 8 | HEMA/EHA | 10:1 | 5 |
| 9 | HEMA/MAA/EHA | 10:1:0.5 | 5 |
| 10 | HEMA/MAA/EHA | 5:1:1.2 | 5 |
| 11 | HEMA/MAA/BA | 10:1:0.5 | 5 |
| Comparative 1 | HEMA/AA | 2:1 | 4 |
| Comparative 2 | HEMA/AA | 1:1 | 4 |
| Comparative 3 | HEMA/MMA | 2:1 | 4 |
| Comparative 4 | HEMA/MMA | 1:1 | 4 |
| Comparative 5 | HEMA/BA | 5:1 | 4 |

TABLE 1-continued

| Example No. | Polymer | Molar ratio of monomers | Dry skin lubricity number |
|---|---|---|---|
| Comparative 6 | HEMA/BA | 2:1 | 3 |
| Comparative 7 | HEMA/MA | 2:1 | 4 |
| Comparative 8 | HEMA/IA | 2:1 | 4 |
| Comparative 9 | HEMA/EHA | 2:1 | 4 |
| Comparative 10 | HEMA/EHA | 1:1 | 4 |
| Comparative 11 | MMA/VPd | 1:1 | 3 |
| Comparative 12 | HEMA | — | 3–4 |
| Comparative 13 | HEA | — | 3–4 |
| Comparative 14 | Vpd | — | 2 |
| Comparative 15 | HPMA | — | 3–4 |
| Comparative 16 | HEMA/HEA | 1:1 | 4 |
| Comparative 17 | HEMA/VPd | 1:1 | 3–4 |
| Comparative 18 | HEMA/HPMA | 1:1 | 4 |
| Comparative 19 | HEA/HPMA | 1:1 | 4 |
| Comparative 20 | HEMA/Vpy | 9:1 | 4–5 |

In the above Table, the abbreviations have the following meanings:

| EHA | 2-ethylhexyl acrylate |
|---|---|
| BA | butyl acrylate |
| AA | acrylic acid |
| MMA | methyl methacrylate |
| MA | methyl acrylate |
| IA | itaconic acid |
| Vpd | N—vinyl pyrrolidone |
| HEA | hydroxyethyl acrylate |
| HPMA | hydroxypropyl methacrylate |
| VPy | vinyl pyridine (quaternized) |

It will be seen that the dry skin lubricity for each of the Examples according to the invention was better than that obtained in any of the Comparative Examples (the only comparative sample approaching the lubricity of the samples according to the invention was that of Comparative Example 20, when a quaternized copolymer was used).

In each of the Examples according to the invention, the coating adhered satisfactorily with at most very slight flaking. This also applied to the Comparative Examples, except Comparative Example 14 (where the coating was washed off on wet-stripping).

The dry frictional force and the coefficient of friction for the glove of Example 6, the glove of Example 10 and for a conventional powdered glove are given in the following Table 2.

TABLE 2

| Glove | Dry frictional force | Coefficient of friction |
|---|---|---|
| Example 6 | 48.7 g | 0.20 |
| Example 10 | 53.1 g | 0.218 |
| Conventional powdered | 78.5 g | 0.323 |

The damp skin lubricity number was 2 for Examples 1 to 11 and Comparative Examples 2 to 10, 12, 13, and 15 to 20, and 1 for Comparative Examples 1, 11 and 14.

EXAMPLES 12 to 21

Samples prepared as in Example 10 were posttreated by dipping in solutions of various materials, as identified in the following Table 3.

TABLE 3

| Example No. | Material | Concentration of solution | Damp skin lubricity number |
|---|---|---|---|
| 12 | N—cetylpyridinium chloride (N—CPC) | 5% | 3–4 |
| 13 | N—cetylpyridinium chloride (N-CPC) | 1% | 3–4 |
| 14 | sodium lauryl sulfate | 5% | 3 |
| 15 | sodium lauryl sulphate | 1.0% | 3 |
| 16 | sodium lauryl sulphate | 0.5% | 3 |
| 17 | sodium lauryl sulfate | 0.1% | 2–3 |
| 18 | N,N—dimethyl hexadecylamine | 1% | 3–4 |
| 19 | Ethylene oxide-polyprolyene glycol condensate | 1% | 3 |
| 20 | Distearyl dimethyl ammonium chloride | 1% | 3 |
| 21 | Hexadecyl trimethyl ammonium chloride | 1% | 3–4 |

In each case, the dry slip was substantially unimpaired.

EXAMPLES 22 to 26

Example 12 was repeated, using solutions containing various proportions of N-CPC and also 0.3% medical grade polydimethyl siloxane, as indicated in the following Table 4.

TABLE 4

| Example No. | Percentage N-CPC | Damp skin lubricity number |
|---|---|---|
| 22 | 0.1 | 3 |
| 23 | 0.25 | 3–4 |
| 24 | 0.50 | 4 |
| 25 | 1.0 | 4 |
| 26 | 2.0 | 4 |

Similar results to those of Example 22 were obtained when the percentage of polydimethyl siloxane was 0.05%.

EXAMPLE 27

A series of hand-shaped formers were dipped into a natural rubber latex to produce a thin rubber layer on each former. The rubber layer was leached in hot water and then primed by dipping in dilute sulphuric acid, rinsed, dipped into a caustic soda bath of pH 10.5 containing hydrogen peroxide in an amount sufficient to react with hydrogen sulphide formed in the priming stage. The rubber, still on the formers, was then dipped into a 4% ethanolic solution of a HEMA/MAA/EHA terpolymer with a monomer molar ratio of 5:1:1.2, the solution also containing 5 to 15 parts per hundred (based on the weight of polymer) of partially methylated melamine-formaldehyde resin available commercially as Cymel 373 (as cross-linking agent) and 0.5 to 1.5 parts per hundred (on the same basis) of para-toluene sulphonic acid (as catalyst).

The rubber was then vulcanised and the polymer simultaneously cured (the temperature being raised from 80° to 150° C. over 25 minutes during vulcanisation), the resulting gloves being stripped from the formers.

The stripped gloves were washed with water and then tumbled in an aqueous solution containing 0.75% by weight of N-cetylpyridinium chloride, the solution also containing 0.05% by weight of emulsified silicone. The gloves were finally tumbled dry at 65° C. for 75 minutes.

The resulting gloves had a dry skin lubricity number of 5 and a wet skin lubricity number of 4 on their polymer-coated surfaces (used as the insides of the gloves).

No allergenic or irritant reaction to the gloves was reported, even when the gloves were worn by surgeons with hypersensitive skin.

We claim:

1. A flexible rubber article which has a coating comprising a lubricating hydrogel polymer bonded thereto to provide a surface of said article said surface coming in contact with the user's skin, wherein a member of the group consisting of surfactant materials and long chain fatty amines has been applied to said surface so as to substantially improve the donning lubricity of said surface with respect to damp skin.

2. An article according to claim 1, in which the surfactant material comprises an ionic surfactant.

3. An article according to claim 2, in which said surfactant is cationic.

4. An article according to claim 1, in which said surfactant material is bactericidal.

5. An article according to claim 3, in which said surfactant has an N-hexadecyl group.

6. An article according to claim 5, in which said surfactant is hexadecyl trimethyl ammonium chloride.

7. An article according to claim 5, in which said surfactant is N-cetyl pyridinium chloride.

8. A process for producing an article according to claim 1, which comprises the steps of:
   (a) forming a flexible rubber article by dipping a form in a rubber latex,
   (b) leaching the rubber article in hot water;
   (c) priming the rubber surface of the article on the former by means of a dilute acid,
   (d) rinsing the primed surface in water or aqueous alkali,
   (e) dipping said rubber article, while still on the former, in a solution of a hydrophilic, hydrogel-forming polymer and a curing agent therefor,
   (f) heat drying the resulting coating such that the resulting hydrogel polymer is bonded to said rubber,
   (g) vulcanizing the rubber and simultaneously curing the polymer by the application of heat,
   (h) stripping the resulting article from the former,
   (i) applying a solution of surfactant material containing silicone to said coating of hydrogel polymer, and
   (j) heating the resulting coating of surfactant material so as to fix the slip properties of the coating.

9. An article according to claim 1, wherein said article is a surgeon's glove.

* * * * *